United States Patent [19]

Yuki et al.

[11] Patent Number: 4,780,209

[45] Date of Patent: Oct. 25, 1988

[54] PROCESS FOR CONCENTRATING AND SEPARATING TRYPSIN INHIBITOR AND KALLIDINOGENASE IN HUMAN URINE

[75] Inventors: Yoshikazu Yuki, Kobe; Koichiro Nakanishi, Ashiya; Hajime Hiratani, Sennan, all of Japan

[73] Assignee: Japan Chemical Research Co., Ltd., Kobe, Japan

[21] Appl. No.: 104,634

[22] Filed: Oct. 2, 1987

Related U.S. Application Data

[63] Continuation of Ser. No. 870,083, Jun. 3, 1986, abandoned.

[51] Int. Cl.$^4$ .................... B01D 15/08; C12N 9/64
[52] U.S. Cl. .................... 210/635; 210/656; 435/226; 435/814; 435/815
[58] Field of Search ............ 210/635, 656, 659; 435/226, 814, 815; 530/395, 412, 413, 415, 417, 427, 834

[56] References Cited

U.S. PATENT DOCUMENTS

4,510,248  4/1985  Nakanishi .................... 435/226

FOREIGN PATENT DOCUMENTS

5515   1/1975  Japan .................... 210/656
99191  7/1980  Japan .................... 210/656
6883   1/1984  Japan .................... 210/656
60-260518 12/1985 Japan .................... 210/656

OTHER PUBLICATIONS

Carlson, Enzyme, 18:176 (1974).
Sumi et al., Journal of Physiol. of Japan, 39:53 (1977).
Johnson et al., Hoppe Seyler's Z. Physiol. Chem., 363:1167 (1982).
N. R. Shulman, J.B.C., 213:655 (1955).
T. A. Strup, Scan. J. Clin. Lab. Invest., 11:181 (1959).
G. J. Proksch, J. Lab. & Clin. Med., 79:491 (1972).
Sumi et al., Medicine and Biology, 100(1):37–39 (1980).
Celander et al., Arch. Biochem. Biophys., 55:286 (1955).

*Primary Examiner*—Ernest G. Therkorn
*Attorney, Agent, or Firm*—Bryan, Cave, McPheeters & McRoberts

[57] ABSTRACT

Two components, trypsin and kallidinogenase, in human urine are concentrated simultaneously by allowing human urine at neutral pH, collecting bubbles thus formed to obtain the concentrate of the two components, adjusting the concentrate to weak acidity, contacting the acidified concentrate with chitosan to allow the two components to be adsorbed onto chitosan, eluting the components from the adsorbent with aqueous ammonia solution, and neutralizing and heating the eluate at about 60° C. for about 10 hours to make the eluate virus-free, followed by separating the components from the eluate.

11 Claims, 1 Drawing Sheet

STABILITY OF HUTI AND HUKN
(Heated at 60°C for 10 hrs. at each pH)

STABILITY OF HUTI AND HUKN (Heated at 60°C for 10 hrs. at each pH)

PROCESS FOR CONCENTRATING AND SEPARATING TRYPSIN INHIBITOR AND KALLIDINOGENASE IN HUMAN URINE

This is a continuation of U.S. application Ser. No. 870,083, filed June 3, 1986, now abandoned.

TECHNICAL FIELD

This invention relates to a process of producing human urine trypsin inhibitor (hereinafter referred to briefly as "HUTI") and human urine kallidinogenase (hereinafter referred to briefly as "HUKN") on an industrial scale and in improved yields, by concentrating simultaneously HUTI and HUKN contained in urine.

BACKGROUND OF THE INVENTION

Urine trypsin inhibitors which are a kind of enzymatic activity inhibitor contained in urines of mammalians are known to vary in characteristic properties depending upon the species of animals from which they are derived [Carlson, Enzyme, 18, 176 (1974)]. HUTI, a glucoprotein having a molecular weight of 68,000 and an isoelectric point of pH 2 to 3, inhibits particularly trypsin, chymotrypsin, plasmin [Sumi, et al., Journal of Physiol. of Japan, 39, 53 (1977)], human esterase [Johnson et al., Hoppe Seyler's Z. Physiol. Chem., 363, 1167 (1982)], etc., and is possibly considered to have application as an anti-inflammatory agent. Kallidinogenase is a proteolytic enzyme produced in every part of the living bodies of animals, and, through its decomposition of kininogen in serum to produce kinin, demonstrates diverse activities, such as blood pressure decreasing and blood flow increasing activities. Both HUTI and HUKN have previously been separated from different species of animals than man, and attempts have been made to utilize them as drugs. Especially, kallidinogenase, which has been produced by using porcine pancreas and urine as raw materials. However, these are proteins foreign to man and exhibit antigenicity. When they are used clinically, frequent administration often produces anaphylaxis, and the problem has been encountered from the standpoint of safety. In contrast to this, HUTI and HUKN are proteins of human origin, and consequently, are entirely free from the aforementioned side effects in humans.

Conventional concentration purification methods for HUTI include, for example, the precipitation method involving the combined use of trichloroacetic acid, ammonium sulfate and methanol [N. R. Shulman: J. B. C., 213, 655 (1955)], the method utilizing bentonite [T. A. Strup: Scan. J. Clin. Lab. Invest., 11, 181 (1959)] and the method using DEAE-cellulose [G. J. Proksch: J. Lab & Clin. Med., 79, 491 (1972)]. With reference to the conventional concentration purification method for HUKN, there are known, for example, the method using silica gel (Japanese Patent Application laid-open No. 99151/1980) and the method utilizing a microporous type of ion exchange resin, such as WA-30 (Japanese Patent Application laid-open No. 5515/1975) as well as the concentration purification method for HUKN developed by the present inventors (Japanese Patent Application laid-open No. 6883/1984) which consists of using chitosan as an adsorbent. A known method of concentrating simultaneously both HUTI and HUKN, is the method of Sumi et al. [Sumi, et al.: Medicine and Biology ("Igaku to Seibutsugaku", vol. 100 (1) (1980)] which involves the use of Arginine-Sepharose. Referring to the above-mentioned methods, those intended for use in the purification and processing into preparations of either HUTI or HUKN alone are not always satisfactory in terms of cost incurred and operation involved. The method of concentrating simultaneously both of these requires too much expensive adsorbent and requires too complex an operational procedure to be practiced on an industrial scale.

DESCRIPTION OF THE INVENTION

The present inventors have found that bubbling takes advantage of the fact that HUTI and HUKN contained as an active ingredient in urine are amphoteric proteins, and that by allowing both HUTI and HUKN to rest on bubbles both HUTI and HUKN can be concentrated. The method has been utilized for concentrating urokinase, a urine enzyme (Celander, DR, Langlinais, R. P. and Guest, M. M.; Arch. Biochem. Biophys., 55, 286 (1955)), but has never been known as a method of concentrating urine kallikrein and urine trypsin inhibitor. Such being the case, bubbling was carried out at different pH values to concentrate urine, and the concentrated urines were comparatively investigated to ascertain the recovery rates of HUKN and HUTI.

In determining the pH of urine to be tested, the following tow factors were taken into consideration:
(1) HUTI undergoes degradation into fractions with smaller molecular weights, when maintained at a pH of below 5.0.
(2) HUKN is unstable at a pH of below 4.0.

Taking the aforementioned factors into account, 60 l of the urine of a lot was divided into 10-l portions, which were adjusted with either 6N-HC or 6N-NaOH to pH 5.0 to 10.0 (precipitates, whenever they separated out, were removed) and then filled into respective columns of 14 in diameter×100 cm in height (each column had a porous plate of 5 mm in diameter provided at the lower flange); air was introduced into the columns by means of a compressor-pump to generate fine bubbles, and the bubbles which overflowed out of the columns were collected, followed by recovery of about 2 l of concentrated urine; and, the recovery ratios for HUTI and HUKN were calculated, with the results being obtained as shown in Table 1.

TABLE 1

| | Yields in relation to pH value | |
|---|---|---|
| | Yield | |
| pH | HUTI | HUKN |
| 5 | 62% | 58% |
| 6 | 74% | 78% |
| 7 | 85% | 88% |
| 8 | 69% | 71% |
| 9 | 58% | 53% |
| 10 | 40% | 38% |

Note:
The urines, at a pH of above 8.0, produced precipitates of mucopolysaccharides, and after the precipitates were removed, bubbling was effected.
The recovery ratios were calculated on the basis of the HUTI and HUKN activities in the original urine without pH adjustment being taken as 100%.

The above results indicate that when bubbling is effected at a pH value of 6.0 to 8.0, preferably in the neighborhood of 7.0 and concentration is completed when the concentrate corresponds to one-fifth the starting volume of the raw urine, HUTI and HUKN can be recovered in a efficient way (under these conditions, uropepsin was not concentrated, but was found to be present at the same level of concentration as in the raw urine).

The present inventors conducted further research, whereupon comparative investigation was performed, by the following procedure and with use of such concentrated urines, on a variety of inorganic adsorbents, ion exchange materials and protein coagulants for the purification degree through adsorption for HUTI and HUKN.

In treating the concentrated urine with each of the above materials, (1) 2% of the concentrated urine was added to each of the materials, and (2) The pH was maintained at a pH value of above 5.0 in order to prevent HUTI from degrading into lower-molecular-weight fractions by the action of uropepsin present in the concentrated urine.

Using the procedure described above, 75 l of urine was concentrated to 15 l (whereby the recovery ratios for HUTI and HUKN were found to be 84% and 89%, respectively). The concentrated urine was divided into 1-l portions, which were subjected to adsorption with 20 g each of the materials, followed by elution. The eluates were dialyzed adequately with water, and the amounts of HUTI, HUKN and protein in the dialyzed eluates were determined. The recovery ratio based on the concentrated urine, along with specific activity, was calculated, with the results being shown in Table 2.

specific activity of HUKN is decreased to about one-fourth, which means that conversely, HUTI contained in large amounts in urine was simultaneously adsorbed onto chitosan, followed by elution.

The eluate obtained after treatment with chitosan as described above was tested for the heat-stability under conditions of 60° C. for 10 hours.

DESCRIPTION OF THE PREFERRED EMBODIMENTS

Figure 1:
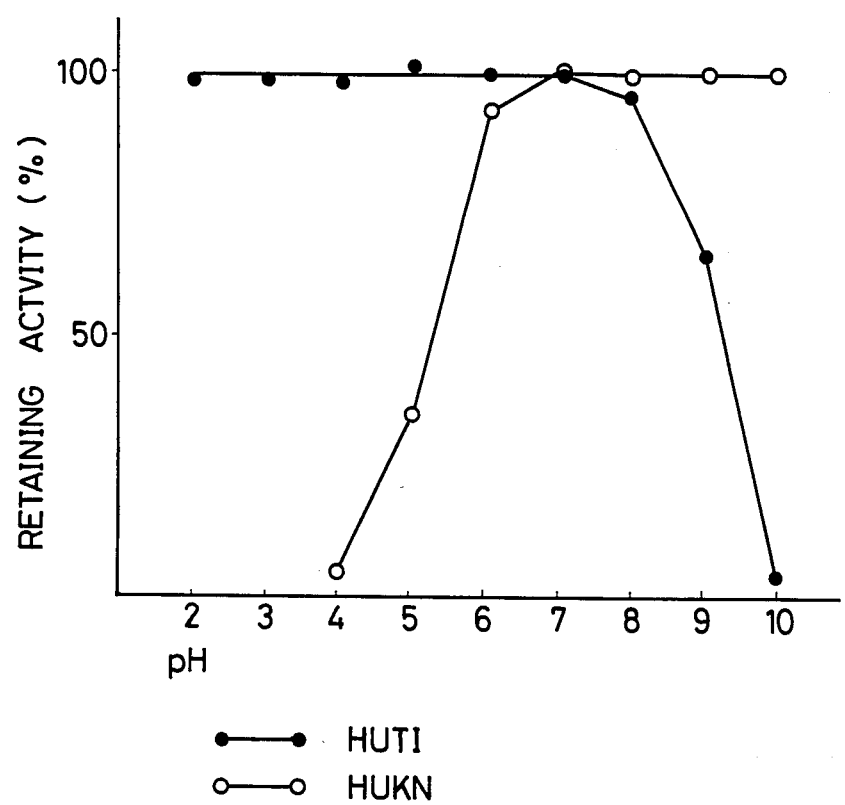
FIG. 1 graphically represents respectively the HUTI and HUKN activities retained for the eluate when adjusted to pH 2–10, and heated at 60° C. for 10 hours.

As is evident from FIG. 1, HUTI and HUKN in the extract obtained by treatment with chitosan of the concentrated urine through bubbling both exhibit maximum heat stability under the conditions of 60° C. and 10 hours only at a pH value of 6 to 8, preferably in the neighborhood of 7.0.

The heat treatment under the conditions of 60° C. and 10 hours has been conventionally adopted for virus sterilization of human urine urokinase preparations.

To subject the extract of this invention to such a heat treatment means to perform simultaneous virus steriliza-

TABLE 2

Screening of adsorption materials for HUTI and HUKN

| No. | Adsorbent | Tested pH | Eluting liquid | Yield, % HUTI | Yield, % HUKN | Spec. activity* HUTI | Spec. activity* HUKN | Supplier |
|---|---|---|---|---|---|---|---|---|
| 1 | Kaolin | 5.0 | 2% aq. ammonia | 4 | 32 | 128 | 6.5 | Wako[1] |
| 2 | Bentonite | 5.0 | 2% aq. ammonia | 63 | 3 | 150 | 2.3 | " |
| 3 | Acid clay | 5.0 | 2% aq. ammonia | 34 | 28 | 121 | 3.1 | " |
| 4 | Silica gel | 5.0 | 2% aq. ammonia | 0 | 51 | — | 9.0 | " |
| 5 | Activated alumina | 5.0 | 2% aq. ammonia | 5 | 10 | 102 | 3.2 | " |
| 6 | Chitosan | 5.0 | 2% aq. ammonia | 71 | 83 | 311 | 8.7 | Kyowa[2] |
| 7 | Amberlite XAD-7 | 7.0 | 2% aq. ammonia | 30 | 21 | 77 | 3.4 | Rohm & Haas |
| 8 | DEAE-cellulose | " | 0.1M H$_3$PO$_4$— 0.5M NaCl pH 7.5 | 51 | 55 | 146 | 4.8 | Braun & Co. (W.G.) |
| 9 | DEAE-Sephadex | " | 0.1M H$_3$PO$_4$— 0.5M NaCl pH 7.5 | 42 | 60 | 121 | 4.3 | Pharmacia Japan |
| 10 | QAE-Sephadex | " | 0.1M H$_3$PO$_4$— 0.5M NaCl pH 7.5 | 62 | 41 | 159 | 3.3 | Pharmacia Japan |
| 11 | Arginine-Sepharose | " | 2% aq. ammonia | 62 | 60 | 205 | 6.6 | Pharmacia Japan |

Note:
*in unit/mg (protein)
[1]Wako Pure Chemical Industries, Ltd. of Japan
[2]Kyowa Oils & Fats Ind., Ltd. of Japan On the basis of the above-described results, it was found that the adsorbent capable of simultaneously recovering HUTI and HUKN in yields of 60% includes chitosan under No. 8 and arginin-Sepharose under No. 15. With regard to the chitosan adsorbent, the present inventors have filed an application for patent (Japanese Patent Application laid-open No. 6883/1984) covering its use for adsorption of HUKN, and it was furthermore found on the basis of the above results that adjustment at pH 5.0 of the concentrate through bubbling and addition of chitosan in amounts of not less than 2% (W/V) can permit HUTI as well as HUKN to be extracted in improved yields. In return for this, nevertheless, the tion of HUTI and HUKN, and this provides great advantages in processing both of them into preparations.

This invention is based on the above findings, and is directed to a process which comprises allowing human urine at a substantially neutral pH to bubble, collecting the resulting bubbles to thereby simultaneously concentrate trypsin inhibitor and kallidinogenase in human urine, adjusting the pH of concentrate to weak acidity, contacting the acidified concentrate with chitosan to allow the both components to be adsorbed simultaneously onto chitosan, subsequently eluting the both components simultaneously from the adsorbent with aqueous ammonia solution, neutralizing the eluate, and heat-treating the neutralized eluate at about 60° C. for about 10 hours, followed by separating the both components from the heat-treated eluate, if desired.

In performing concentration by means of the bubbling method, it is desirable to adjust human urine to pH 6.0 to 8.0, preferably pH 7.0, and it is advisable to concentrate human urine to a concentrated volume of about one-fifth that of original starting volume of the raw, urine. The concentrate, which is to be contacted with chitosan, is desirably adjusted to pH 4.5 to 6.5, preferably pH 5.5. It is preferred to use chitosan in the amount of 20 to 30 g per liter of the concentrate, namely 2 to 3% (w/v), preferably about 25 g, namely about 2.5% (w/v).

HUTI and HUKN in the concentrate are selectively adsorbed onto chitosan by contacting the concentrate with chitosan. The adsorbent material is then collected by filtration and washed with water, if necessary, and HUTi and HUKN are desirably eluted with aqueous ammonia, at a pH of from about 10.5–12.0.

If desired, the resulting eluate is adjusted to a pH value of 6 to 8, preferably at pH 7.0, with 6N HCl and heat-treated at 60° C. for 10 hours, and HUTI and HUKN can be separated from each other and collected by means of affinity chromatography such as aprotinin-affinity chromatography and trypsin-affinity chromatography.

According to this invention, HUTI and HUKN can be concentrated efficiently by the bubbling method, whereupon chitosan is an adsorbent capable of selectively adsorbing both of the components in the resulting concentrated urine at a specifically stated pH value, and 2N to 3N aqueous ammonia acts as an eluting liquid for simultaneously desorbing both components. Heat treatment of the resulting eluate at a pH value in the neighborhood of neutrality at 60° C. for 10 hours results in a virus sterilized product useful for processing into preparations. These actions cooperate with each other to permit both components in human urine to be concentrated and separated in a simplified manner.

According to this invention, there is provided a process wherein HUTI and HUKN, physiologically active substances in human urine, are concentrated and purified simultaneously and efficiently on an industrial scale. The heat-treatment at about 60° C. for about 10 hours performed in the process to make the concentrated or purified material virus-free facilitates the subsequent processing into preparations. Therefore, it is an outstanding economiclal process for directly handling a large amount of urine.

The following examples illustrate the present invention in more detail.

EXAMPLE 1

A 10-liter portion of urine from a healthy male adult is adjusted to pH 7.0 and added into a column (which has a porous plate of 5 mm in diameter provided at the lower flange of the column) of 14 cm in diamter and 100 cm in height, and air is introduced by a compressor-pump into the column from the bottom end to perform bubbling. The resulting bubbles are received in another vessel, and when the volume of the liquid produced after the bubbles have crushed reaches the volume of about 2 l, the bubbling is completed and the urine concentrated. 2N-HCl is added to the concentrate to adjust the pH to 5.0, and 50 g of chitosan is added to it, followed by stirring for 1 hour to adsorb HUTI and HUKN. The chitosan is collected by filtration and washed with water, and both components are eluted with 2N aqueous ammonia to yield 150 ml of the eluate. The resulting eluate is adjusted to pH 6.5 with 6N-HCl and heat-treated at 60° C. for 10 hours to yield 148 ml of the treated liquid. The liquid exhibits total HUTI activity of 47,200 inhibitory units (recovery ratio of 61%) and purity of 310 inhibitory units/mg (protein), and total HUKN activity of 1,245 units (recovery ratio of 70%) and purity of 8.2. units/mg (protein).

EXAMPLE 2

A 20-liter portion of urine from a healthy male adult is adjusted to pH 6.5, and filled into a column of 20 cm in diameter and 100 cm in height having a porous plate similar to that of Example 1, followed by bubbling. The resulting bubbles are received in another vessel, and when about 4 l of the liquid is collected, the bubbling is completed and the urine concentrated. 2N-HCl is added to the concentrated urine to adjust to pH 5.5, and 100 g of chitosan is added to it, followed by stirring for 1 hour to adsorb HUTI and HUKN. The chitosan is collected by filtration and washed with water, and the adsorbed substances are eluted with 3N aqueous ammonia. The resulting eluate of 300-ml volume is adjusted to pH 7.0 with 6N-HCl and heat-treated at 60° C. for 10 hours to yield 297 ml of the treated liquid. The liquid, when determined for the HUTI activity, is found to exhibit total HUTI activity of 95,200 inhibitory units (recovery ratio of 60%) and purity of 302 inhibitory units/mg (protein), and determination of the HUKN activity shows that it possesses total HUKN activity of 2,789 units (recovery ratio of 72%) and purity of 8.9 units. The liquid does not show any decrease in the activity of either of the active substances, even after storage at 5° C. (in a refrigerator) for 1 week.

EXAMPLE 3

The heat-treated extract liquid obtained in Example 2 is dialyzed against 0.5M sodium chloride-0.1M sodium hydrogencarbonate buffer pH 8.0, and passed through a column consisting of an aprotinin-Sepharose (refer to the note 1, below) column (with a diameter of 3.0 cm and a height of 15 cm) equilibrated with the same buffer being connected with a trypsin-Sepharose (refer to the note 1, below) column (with a diameter of 3.0 cm and a height of 15 cm). The aprotinin-Sepharose column is subjected to elution with 0.1M acetic acid buffer (pH 3.5) containing 0.5M sodium chloride to yield 41 ml of the HUKN eluate. The trypsin-Sepharose column is subjected to elution with glycine hydrochloric acid buffer pH 2.6 containing 0.5M sodium chloride to yield 48 ml of the HUTI eluate. The eluate exhibits total HUTI activity of 74,580 inhibitory units (recovery ratio of 47%) and purity of 1,1320 inhibitory units/mg (protein), being entirely free from HUKN. The HUKN eluate shows total HUKN activity of 2,130 units (recovery ratio of 55%) and purity of 825 units/mg (protein), being entirely free from HUTI.

EXAMPLE 4

Following the method described in Example 2, 309 ml of heat-treated extract uses obtained. The extract exhibited total HUTI activity of 93,100 inhibitory units (recovery ratio of 63%) and purity of 311 inhibitory units/mg (protein), together with total HUKN activity of 2,698 units (recovery ratio of 73%) and purity of 9.0 units/mg (protein). The extract is dialyzed against 0.5M sodium chloride-0.05M phosphate buffer pH 8.5, and the dialyzate is passed through an aprotinin-Sepharose column and trypsin-Sepharose column, as described in Example 3, after having been equilibrated adequately with the above-described buffer. The aprotinin-Sepharose column is subjected to elution with 0.1M acetic acid buffer (pH 3.5) containing 0.5M sodium chloride to give 46 ml of the HUKN eluate. The trypsin-Sepharose column is subjected to elution with glycine hydrochloric acid buffer (pH 2.3) containing 0.5M sodium chloride to yield 52 ml of the HUTI eluate. The HUKN eluate exhibits total HUKN activity of 2,053 units (recovery ratio of 53%) and purity of 831 units/unit (protein, being entirely free from HUTI. The HUTI eluate shows total HUTI activity of 66,500 inhibitory units (recovery ratio of 45%) and purity of 1,290 inhibitory units/mg (protein), being totally free from HUKN. The HUTI and HUKN eluates thus obtained are both found to show no decrease in titer, even after being stored at 4° C. for 2 weeks subsequent to neutralization and sterile filtration.

In Examples 1 to 4, the HUTI inhibitory unit is determined by means of the method of Tanaka et al. [Biochimica et Biophysica Acta, 705, 192 (1982)]; the employed trypsin is bovine trypsin type I manufactured by Sigma Co. As to the HUKN inhibitory unit, the HUKN extracted for purification from human urine by the present inventors is subjected to determination of the inhibitory units by means of the vasodilator assay [J. Biochemistry, 58, 201 (1965)], and using the HUKN as a standard, HUKN inhibitory units are determined by the fluorescent synthetic substrate method [J. Biochemistry, 82, 1495 (1977)]. The protein amount is determined by use of the Lowry-Folin method using bovine serum albumin as a standard.

[Note 1]:

Preparation of trypsin-Sepharose and aprotinin-Sepharose:

Trypsin-Sepharose and aprotinin-Sepharose are prepared from trypsin type I [Sigma Co. of U.S.A.], aprotinin [Choay Co. of France] and CNBR activated Sepharose 4B [Pharmacia Japan[ by means of P. Cuatrecasas' method [J. Biol. Chem., 245, 3095 (1970)].

What is claimed is:

1. A method of concentrating and separating human urine trypsin inhibitor and human urine kallidinogenase, comprising the steps of
   (1) bubbling human urine at a substantially neutral pH;
   (2) collecting the bubbles formed in step (1) to thereby simultaneously concentrate trypsin inhibitor and kallidinogenase from said urine;
   (3) adjusting the concentrate to a weakly acidic pH;
   (4) contacting the pH adjusted concentrate of step (3) with chitosan to thereby simultaneously adsorb both trypsin inhibitor and kallidinogenase on the chitosan;
   (5) eluting the adsorbed trypsin inhibitor and kallidinogenase from the chitosan with an aqueous ammonia solution;
   (6) neutralizing the eluate; and
   (7) heat-treating the neutralized eluate at about 60° C. for about 10 hours.
2. The process of claim 1, wherein the urine is adjusted to a pH of 6.0–8.0.
3. The process according to claim 2, wherein human urine is bubbled at pH 7.
4. The process of claim 1, wherein the concentrate is adjusted to a pH of 4.5–6.5 prior to contacting the concentrate with chitosan.
5. The process according to claim 4, wherein the concentrate is bubbled at pH 5.5.
6. The process of claim 1, wherein the aqueous ammonia solution has a pH of 10.5–12.0.
7. The process of claim 1, wherein the concentrate is contacted with not less than 2% (w/v) of chitosan, and the elution from the chitosan is carried out with an aqueous ammonia solution having a pH of 10.5–12.0.
8. The process according to claim 7, wherein the concentrate is contacted with 2.5% (w/v) of chitosan, and the elution is carried out with an aqueous ammonia solution at pH 10.5–12.
9. The process according to claim 1, wherein the eluate is neutralized to a pH of 6.0–7.5, followed by heat treatment at about 60° C. for 10 hours.
10. The process according to claim 9, wherein the eluate is neutralized to pH 7, and then heat treated at about 60° C. for about 10 hours.
11. The process of claim 1, and further comprising the step of separating the trypsin inhibitor from kallidinogenase.

* * * * *